US00PP37650P2

(12) United States Plant Patent
Moucheboeuf

(10) Patent No.: US PP37,650 P2
(45) Date of Patent: Aug. 25, 2026

(54) ***DIANTHUS* PLANT NAMED 'KLEDA25852'**

(50) Latin Name: ***Dianthus* x *allwoodii* hort**
Varietal Denomination: KLEDA25852

(71) Applicant: KLEMM + SOHN GMBH & CO. KG, Stuttgart (DE)

(72) Inventor: Laetitia Moucheboeuf, Exeter (GB)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/319,132

(22) Filed: Sep. 4, 2025

(51) Int. Cl.
*A01H 5/02* (2018.01)

(52) U.S. Cl.
USPC ..... Plt./273

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Weatherly IP Solutions, LLC; Karen P. Bechtold; James M. Weatherly

(57) ABSTRACT

A new *Dianthus* plant named 'KLEDA25852' particularly distinguished by many flower stems per plant, a compact and dense plant base, and a white flower color with burgundy macule, is disclosed.

1 Drawing Sheet

Genus and species: *Dianthus* x *allwoodii* hort.
Variety denomination: 'KLEDA25852'.

BACKGROUND OF THE NEW PLANT

The present invention comprises a new and distinct variety of *Dianthus*, botanically known as *Dianthus* x *allwoodii* hort. and hereinafter referred to by the variety name 'KLEDA25852'. 'KLEDA25852' originated from an open cross pollination between the proprietary female parent 'PIE.134' (unpatented) and an unknown male parent between May 2018 and August 2018.

In June 2019, 'KLEDA25852' was selected and in September 2019, 'KLEDA25852' was first vegetatively propagated by vegetative cuttings in Ashcombe, Dawlish, United Kingdom. 'KLEDA25852' was found to reproduce true to type in successive generations of asexual propagation in Stuttgart, Germany via vegetative cuttings.

SUMMARY

The following are the most outstanding and distinguishing characteristics of 'KLEDA25852' when grown under normal horticultural practices in Stuttgart, Germany.

1. many flower stems per plant,
2. a compact and dense plant base, and
3. a white flower color with burgundy macule

DESCRIPTION OF THE PHOTOGRAPH

This new *Dianthus* plant is illustrated by the accompanying photograph of a 9-month-old plant taken in June 2023 indoor in Dawlish Devon, United Kingdom. The colors shown are as true as can be reasonably obtained by conventional photographic procedures. The photograph is a whole plant photo of 'KLEDA25852' and shows the foliage, buds, and flowers.

DESCRIPTION

The following detailed descriptions set forth the distinctive characteristics of 'KLEDA25852'. The data which define these characteristics were collected from asexual reproductions carried out in Dawlish, United Kingdom. Data was collected in June 2025 from 9-month-old plants grown in a greenhouse. Color references are to The R.H.S. Colour Chart of The Royal Horticultural Society of London (R.H.S.), 6$^{th}$ edition (2015).

Classification:
- *Family*.—Caryophyllaceae.
- *Botanical*.—*Dianthus* x *allwoodii* hort.
- *Designation*.—'KLEDA25852'.
- *Type*.—Perennial carnation.

Parentage:
- *Female parent*.—'PIE.134' (unpatented).
- *Male parent*.—Unknown.

Plant:
- *Propagation type*.—Vegetative cuttings via shoot cuttings.
- *Time to produce a rooted young plant*.—5 weeks to produce a rooted plug.
- *Root description*.—Fibrous, fine roots; RHS 156D.
- *Rooting habit shape*.—Fibrous.
- *Plant form*.—Compact mounding, upright.
- *Plant height*.—34.0 cm to 38.0 cm.
- *Plant diameter or spread*.—18.0 cm to 22.0 cm.

Lateral branches/stems (shoot before elongation):
- *Shape of the branch in cross-section*.—Circular.
- *Hollowness of the branch*.—Absent.
- *Length*.—10.0 cm to 12.0 cm.
- *Diameter*.—0.4 cm.
- *Internode length*.—0.3 cm to 0.5 cm.
- *Internode quantity per branch*.—5 to 6.
- *Number of internodes per branch/stem*.—5 to 6.
- *Node length*.—0.2 cm to 0.3 cm.
- *Node diameter*.—0.3 cm.
- *Texture*.—Smooth.
- *Color (in sheathing zone)*.—Between RHS 145B and RHS 145D.

Lateral branches/stems (Flower stem):
- *Number of flower stems per plant*.—4 to 6.
- *Shape of the branch in cross-section*.—Circular.

*Hollowness of the branch*.—Absent.
*Length*.—30.0 to 34.0 cm.
*Diameter*.—0.2 cm.
*Internode length*.—1.0 cm to 7.0 cm.
*Internode quantity per branch*.—5 to 6 up to breaking point of flower stem.
*Node length*.—0.4 cm to 0.5 cm.
*Node diameter*.—0.4 cm to 0.5 cm.
*Texture*.—Smooth.
*Color*.—RHS N189C.
*Flower clustering on the lateral branch*.—None.

Foliage:
*Arrangement*.—Opposite, sheathing and spiraling up the stem.
*Length*.—10.0 to 12.0 cm.
*Width*.—0.4 cm.
*Shape*.—Linear.
*Apex*.—Acute.
*Base*.—Decurrent.
*Margin*.—Entire.
*Texture* (*both upper and lower surfaces*).—Smooth.
*Cross-section of the leaf*.—Weakly concave.
*Curvature of the leaf*.—Absent or very weakly concave.
*Glaucosity of the leaf*.—Medium to strong.
*Leaf color* (*both immature and mature*).—Immature: Upper surface: RHS 189B. Lower surface: RHS 189B. Mature: Upper surface: RHS 189A. Lower surface: RHS 189A.
*Venation pattern*.—Absent.

Flowers:
*Flower type and habit*.—Single and round.
*Fragrance*.—Present, and sweet smelling.
*Position of the flowers compared to the foliage of the plant*.—Far above.
*Profile of both the upper and lower part in the lateral view*.—Flat.
*Diameter of the flower*.—5.0 to 5.5 cm.
*Natural flowering season*.—Spring to Autumn.
*Number of flowers per spray*.—5 to 10.
*Flower longevity on the plant*.—10 to 20 days.

Buds (before cracking color):
*Length*.—3.0 cm.
*Diameter*.—0.8 cm.
*Shape*.—Oblong.
*Color*.—Upper part RHS189B, lower part RHS 145A.
*Extrusion of the styles at the bud stage*.—Absent.

Corolla:
*Profile of the upper part of the corolla* (*lateral view*).—Concave.
*Profile of the lower part of the corolla* (*lateral view*).—Flat convex.
*Quantity of petals and arrangement*.—5 petals, persistent, apopetalous and overlapping.
*Corolla height*.—0.5 to 1.0 cm.
*Petal length*.—5.0 to 5.2 cm.
*Petal width*.—3.3 to 3.5 cm.
*Petal shape*.—Fan shaped.
*Petal apex*.—Obtuse.
*Petal base*.—Acute.
*Petal margin*.—Dentate.
*Depth of petal margin*.—Medium.
*Petal texture* (*both upper and lower surfaces*).—Smooth.
*Petal color*.—Immature: Upper surface: RHS NN155D. Lower surface: RHS NN155D. Mature: Upper surface: RHS NN155D. Lower surface: RHS NN155D.
*Macule*.—Present: 0.7 cm wide and RHS 187B and RHS 187C with a slight hue at the base of the macule RHS145D.

Calyx:
*Quantity of sepals and arrangement*.—Composed of 5 sepals, fused up to 1 cm below the apex.
*Longitudinal axis of the lobes of the calyx*.—Straight.
*Shape*.—Cylindrical.
*Calyx height*.—3.0 cm.
*Calyx diameter* (*at the apex*).—1.0 cm.
*Approximate length of the calyx lobe*.—0.2 cm.
*Sepal texture* (*both upper and lower surfaces*).—Smooth.
*Sepal color*.—Upper surface: RHS N138B at the apex and RHS 144D at the base. Lower surface: RHS 144D.
*Position of the outer lobes of the epicalyx in relation to the calyx*.—Adpressed and free.
*Apex shape of the outer lobes of the epicalyx*.—Acute.
*Approximate tip length of outer epicalyx lobes*.—0.5 cm.
*Position of the inner lobes of the epicalyx in relation to the calyx*.—Adpressed.
*Apex shape of the inner lobes of the epicalyx*.—Short acuminate.
*Approximate tip length of inner epicalyx lobes*.—1.5 cm.

Peduncles:
*Length*.—30.0 to 34.0 cm.
*Diameter*.—0.2 cm.
*Strength*.—Strong.
*Texture*.—Smooth.
*Color*.—RHS N189 C.

Reproductive organs:
*Stamens*.—Quantity per flower: 10. Filament length: 3.0 to 3.3 cm. Filament color: RHS NN155C. Anther length: 0.4 cm. Anther diameter: 0.1 cm. Anther color: RHS N75D (before dehiscence). Anther attachment and shape: Dorsifixed, linear. Pollen amount: High.
*Pistils*.—Quantity per flower: 1 (2 styles). Length: 3.5 to 4.0 cm.
*Stigma*.—Color: RHS NN155B. Shape: Linear and hairy along the style. Length: 2.5 to 3.0 cm. Diameter: 0.1 cm.
*Style*.—Color: RHS NN155B. Length: 1.0 to 1.5 cm, along the stigma. Diameter: 0.1 cm. Shoulder: Absent.
*Ovary*.—Size: 1.0 cm in length and 0.9 cm in diameter. Shape: Rhombic. Color: RHS 145B on the apical half and RHS 145D on the basal half. Texture: Smooth.

Seeds:
*Size*.—0.4 cm in length, 0.3 cm in width.
*Color*.—RHS 202A.
*Shape*.—Oval and flattened.
*Amount*.—Low to medium.

Disease and insect resistance: No particular disease or insect resistance observed.

COMPARISON OF 'KLEDA25852' WITH PARENTAL LINE AND KNOWN VARIETY

'KLEDA25852' is distinguished from the known female parent as described in Table 1.

TABLE 1

| Comparison with Parental Line | | |
|---|---|---|
| Trait or characteristic | 'KLEDA25852' | 'PIE.134' (unpatented) |
| Amount flower stems per plants | More than 'PIE. 134' | Less than 'KLEDA25852' |
| Plant base | Compact and dense | Open and thin |

'KLEDA25852' can be compared to the commercial *Dianthus* variety 'WP22 PIE39' (U.S. Plant Pat. No. 35,561). Differences between the varieties are described in Table 2.

TABLE 2

| Comparison with Similar Variety | | |
|---|---|---|
| Trait or characteristic | 'KLEDA25852' | 'WP22 PIE39' (U.S. Plant Pat. No. 35,561) |
| Flower color | White with burgundy macule | White with magenta macule |

I claim:

1. A new and distinct variety of *Dianthus* plant designated named 'KLEDA25852' as shown and described herein.

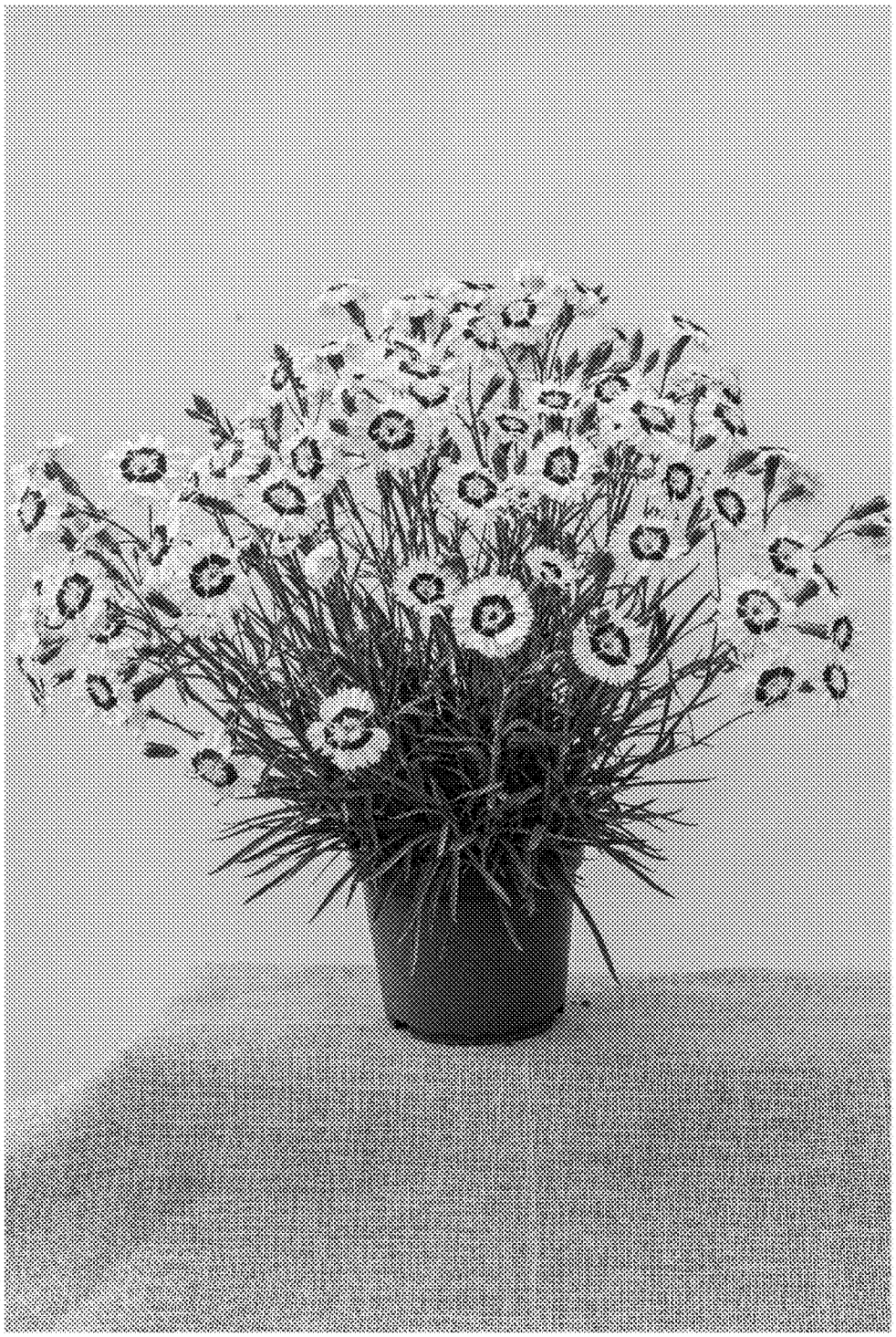

* * * * *